United States Patent [19]

Kirkland et al.

[11] Patent Number: 4,683,228

[45] Date of Patent: Jul. 28, 1987

[54] GUANIDINOPYRAZOLYLAMIDES, GUANIDIMOIMIDAZOLYLAMIDES, COMPOSITIONS CONTAINING THEM, AND METHOD OF USING THEM TO INHIBIT GASTRIC ACID SECRETION

[75] Inventors: Karin M. Kirkland, Wilmington, Del.; Derrick M. Mant, Stockport, England

[73] Assignees: ICI Americas Inc., Wilmington, Del.; Imperial Chemical Industries PLC, London, England

[21] Appl. No.: 693,179

[22] Filed: Jan. 22, 1985

[30] Foreign Application Priority Data

Jan. 24, 1984 [GB] United Kingdom ................. 8401751

[51] Int. Cl.$^4$ ..................... A61K 31/54; A61K 31/55; C07D 419/12; C07D 419/14
[52] U.S. Cl. .................................... 514/211; 514/212; 514/218; 514/228; 514/230; 514/233; 514/241; 514/242; 514/245; 514/252; 514/269; 514/272; 514/274; 514/316; 514/318; 514/326; 514/340; 514/341; 514/359; 514/361; 514/362; 514/363; 514/364; 514/365; 514/369; 514/370; 514/372; 514/374; 514/376; 514/377; 514/378; 514/380; 514/383; 514/384; 514/385; 514/397; 514/398; 514/402; 514/403; 514/406; 514/407; 540/544; 540/553; 540/575; 540/596; 540/597; 540/598; 540/601; 540/602; 540/603; 544/2; 544/3; 544/7; 544/8; 544/55; 544/56; 544/58.6; 544/63; 544/66; 544/67; 544/72; 544/82; 544/96; 544/98; 544/111; 544/112; 544/113; 544/114; 544/120; 544/121; 544/122; 544/124; 544/130; 544/131; 544/132; 544/133; 544/134; 544/137; 544/138; 544/139; 544/140; 544/141; 544/180; 544/182; 544/194; 544/212; 544/213; 544/216; 544/217; 544/218; 544/219; 544/224; 544/238; 544/242; 544/295; 544/296; 544/298; 544/315; 544/316; 544/317; 544/319; 544/320; 544/322; 544/324; 544/326; 544/327; 544/328; 544/329; 544/330; 544/331; 544/332; 544/333; 544/336; 544/357; 544/358; 544/359; 544/360; 544/364; 544/366; 544/367; 544/369; 544/370; 544/371; 544/372; 544/405; 546/187; 546/193; 546/208; 546/209; 546/210; 546/211; 546/255; 546/256; 546/264; 546/275; 546/276; 546/277; 546/278; 546/279; 546/280; 546/281; 546/283; 546/284; 546/306; 546/332; 548/125; 548/127; 548/128; 548/129; 548/130; 548/131; 548/132; 548/133; 548/134; 548/135; 548/136; 548/138; 548/141; 548/143; 548/144; 548/146; 548/182; 548/183; 548/184; 548/187; 548/190; 548/191; 548/194; 548/206; 548/213; 548/214; 548/215; 548/225; 548/226; 548/227; 548/228; 548/229; 548/230; 548/232; 548/233; 548/240; 548/243; 548/244; 548/245; 548/246; 548/247; 548/249; 548/255; 548/262; 548/264; 548/265; 548/266; 548/267; 548/269; 548/300; 548/336; 548/337; 548/342; 548/348; 548/356; 548/374; 548/375; 548/376; 548/377; 548/378; 548/379; 548/517; 548/518; 548/519; 548/521; 548/527; 548/540; 548/541; 548/543; 548/544; 548/550; 548/557; 548/558

[58] Field of Search ............... 548/336, 337, 374, 376, 548/375, 125, 127, 128, 129, 130, 131, 132, 133, 134, 135, 136, 138, 141, 143, 144, 146, 182, 183, 184, 187, 190, 191, 194, 206, 213, 214, 215, 225, 226, 227, 228, 229, 230, 232, 233, 240, 243, 244, 245, 246, 247, 249, 255, 262, 265, 266, 269, 342, 348, 377, 378; 514/211, 212, 218, 228, 230, 233, 241, 242, 245, 252, 269, 272, 274, 316, 318, 326, 340, 341, 359, 361, 362, 363, 364, 365, 369, 370, 372, 374, 376, 377, 378, 380, 383, 384, 385, 397, 398, 402, 403, 406, 407; 540/544, 553, 575, 596, 597, 598, 601, 602, 603; 544/63, 72, 82, 96, 97, 111, 120, 121, 122, 123, 124, 130, 132, 133, 134, 137, 138, 139, 140, 238, 295, 322, 331, 333, 357, 359, 360, 364, 366, 367, 369, 370, 371, 372, 405; 546/187, 193, 208, 209, 210, 211, 275, 276, 277, 278, 279, 548/125, 127, 128, 129, 130, 131, 132, 133, 134, 135, 136, 138, 141, 143, 144, 146, 182, 183, 184, 187, 190, 191, 194, 206, 213, 214, 215, 225, 226, 227, 228, 229, 230, 232, 233, 240, 243, 244, 245, 246, 247, 249, 255, 262, 265, 266, 269, 336, 337, 342, 348, 374, 375, 376, 377, 378

[56] References Cited

U.S. PATENT DOCUMENTS 4,447,441 5/1984 Yellin et al. ...................... 548/265

OTHER PUBLICATIONS

Burger's Medicinal Chem., Edit. by Wolff, 4th Edit., 1981, pp. 537-540 and 507-509.
Medicinal Chem., Edit by Burger, 2nd Edit., 1960, pp. 72-88.

Primary Examiner—Henry R. Jiles
Assistant Examiner—Kurt G. Briscoe
Attorney, Agent, or Firm—Rosemary M. Miano

[57] ABSTRACT

A guanidine derivative of the formula I:

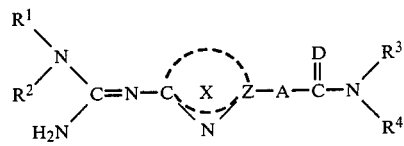

in which $R^1$, $R^2$, $R^3$, $R^4$, ring X and D are a variety of radicals defined in the specification and A is a 3-8C alkylene chain which is substituted by a hydroxy radical and into which is optionally inserted, as part of the backbone of the chain, one or two groups selected from oxygen and sulphur atoms and NH and 1-6C N-alkyl radicals; and the pharmaceutically-acceptable acid addition salts thereof. Pharmaceutical compositions and methods of manufacture are also described. The compound of the formula I is a histamine H-2 antagonist and is therefore useful in ulcer therapy.

14 Claims, No Drawings

GUANIDINOPYRAZOLYLAMIDES, GUANIDIMOIMIDAZOLYLAMIDES, COMPOSITIONS CONTAINING THEM, AND METHOD OF USING THEM TO INHIBIT GASTRIC ACID SECRETION

This invention relates to guanidine derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit.J.Pharmac.*, 1966, 27, 427) and the action of histamine at this receptor is blocked (antagonised) by classical "antihistamine" drugs such as mepyramine. The second histamine receptor has been named the H-2 receptor (Black et al, *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In European Patent Publication No. 60094 there are described histamine H-2 receptor antagonists which are guanidino heterocycles carrying a side chain to the end of which is attached a carbamoyl group. It has now been discovered that if a hydroxy radical is attached to this side chain there are produced potent histamine H-2 receptor antagonists.

According to the invention there is provided a guanidine derivative of the formula I in which $R^1$ and $R^2$, which may be the same or different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of $R^1$ and $R^2$ is a halogen-substituted alkyl, cycloalkyl or cycloalkylalkyl radical and provided there is no halogen substituent on the carbon atom of the alkyl, cycloalkyl or cycloalkylalkyl radical which is directly attached to the nitrogen atom, or $R^2$ is a hydrogen atom and —$R^1$ is a radical of the formula II in which W is an unbranched 2–6C alkylene chain which is optionally substituted by one or two 1–4C alkyl radicals, E is an oxygen or sulphur atom, a sulphinyl or sulphonyl radical, or a radical of the formula $NR^6$ in which $R^6$ is a hydrogen atom or a 1–6C alkyl radical, $R^5$ is a hydrogen atom or an unbranched 1–6C alkyl radical which is optionally substituted by one or two 1–4C alkyl radicals, or $R^5$ and $R^6$ are joined to form, together with the nitrogen atom to which they are attached, a pyrrolidine, piperidine, morpholine, piperazine or N-methylpiperazine ring;

in ring X the dotted line is a double bond on one side of the nitrogen atom and Z is a carbon or nitrogen atom such that ring X is a 5- or 6-membered aromatic heterocyclic ring which contains at least one nitrogen atom and may optionally contain one or two additional hetero atoms selected from oxygen, nitrogen and sulphur atoms, which heterocyclic ring may, where possible, carry one or two optional substituents, the optional substituents on ring X being selected from fluorine, chlorine and bromine atoms and 1–6C alkyl, 1–6C alkoxy, trifluoromethyl, hydroxy and amino radicals;

—A— is a 3–8C alkylene chain which is substituted by a hydroxy radical and into which is optionally inserted, as part of the backbone of the chain, one or two groups selected from oxygen and sulphur atoms and NH and 1–6C N-alkyl radicals, provided that the shortest link between ring X and C═D is of at least 3 atoms, provided that no optional insertion is made in chain A which results in the inserted group being directly attached to C═D, provided that no two insertions are directly attached one to the other, and provided that an inserted atom or radical is not attached to the carbon atom which carries the hydroxy radical;

$D_3$ is an oxygen or sulphur atom;

$R^3$ is a hydrogen atom or a hydroxy, amino, 1–6C alkylamino, 1–6C haloalkylamino, 1–6C alkanoylamino, 1–6C alkyl, 3–8C cycloalkyl, 4–12C cycloalkylalkyl, 2–6C alkenyl, 2–6C alkynyl, 1–6C haloalkyl, 1–6C alkoxy, 1–6C hydroxyalkyl, 2–10C alkoxyalkyl, 2–10C alkylthio-alkyl, 1–6C aminoalkyl, 2–8C alkylaminoalkyl, 3–12C dialkylaminoalkyl, 2–8C alkanoylaminoalkyl, 8–14C aroylaminoalkyl, 3–10 C alkoxycarbonylalkyl, 2-carbamoylalkyl, 6–10aryl, 7–11C arylalkyl, heteroaryl or heteroarylalkyl radicals, wherein the heteroaryl part is a heterocyclic aromatic ring containing one, two or three hetero atoms selected from oxygen, nitrogen and sulphur atoms, wherein the alkyl part of the heteroarylalkyl radical is 1–6C and wherein, when $R^3$ is or contains an aryl or heteroaryl ring, that ring is optionally substituted by one or two groups selected from fluorine, chlorine, bromine and iodine atoms and 1–6C alkyl, 1–6C alkoxy, 1–6C alkylthio, 2–6C dialkylamino, 2–6C alkanoyl, trifluoromethyl, hydroxy and amino radicals;

$R^4$ is a hydrogen atom or $R^3$ and $R^4$ are joined to form, together with the nitrogen atom to which they are attached, a 5-, 6- or 7-membered saturated ring which optionally contains a double bond or an additional oxygen atom, NH or 1–6C N-alkyl radical; and the pharmaceutically-acceptable acid-addition salts thereof.

It is to be understood that, in the above formula I and throughout this specification, although the double bond in the guanidine residue attached to ring X has been inserted in a particular position, other tautomeric forms are possible, and this invention includes such tautomeric forms within its scope, both in terms of the compounds of the invention and in terms of the manufacturing processes. The compound of the formula I contains at least one asymmetric centre, namely the carbon atom in A to which the hydroxy group is attached. The compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for $R^1$ or $R^2$ when it is a halogen-substituted alkyl radical is a 2,2,2-trifluoroethyl, 2,2,2- trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-cloro-1,1,3,3-pentafluoroisopropyl, 1,3-difluoroisopropyl or 2,2,3,3,4,4,4-heptafluorobutyl radical.

A particular value for $R^1$ or $R^2$ when it is a halogen-substituted cycloalkyl radical is a 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl or 2-chloro-2,3,3,4,4-pentafluorocyclobutyl radical.

A particular value for $R^1$ or $R^2$ when it is a halogen-substituted cycloalkylalkyl radical is a (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl or (2-chloro-1,2,3,3,4,4-hexafluorocyclobutyl)methyl radical.

A particular value for $R^1$ or $R^2$ when it is an alkyl radical is a methyl, ethyl, propyl, isopropyl or butyl radical.

A particular value for $R^1$ or $R^2$ when it is a cycloalkyl radical is a cyclopropyl or cyclobutyl radical.

A particular value for $R^1$ or $R^2$ when it is a cycloalkylalkyl radical is a cyclopropylmethyl or cyclobutylmethyl radical.

A particular value for the optional substituent on W is a methyl radical.

A particular value for $R^5$ is a hydrogen atom or a methyl radical.

A particular value for $R^6$ is a hydrogen atom or a methyl radical.

A particular value for the radical of the formula II is a 2-methoxyethyl, 2-hydroxyethyl, 2-methylthioethyl or 2-dimethylaminoethyl radical.

A particular value for ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring, each being optionally substituted, where possible, by one or two substituents selected from fluorine, chlorine and bromine atoms and methyl, methoxy, trifluoromethyl, hydroxy and amino radicals.

A particular value for —A— is a 1-hydroxytrimethylene, 2-hydroxytrimethylene, 3-hydroxytrimethylene, 1-hydroxytetramethylene, 2-hydroxytetramethylene, 3-hydroxytetramethylene, 4-hydroxytetramethylene, 1-hydroxypentamethylene, 2-hydroxypentamethylene, 3-hydroxypentamethylene, 4-hydroxypentamethylene, 5-hydroxypentamethylene, thio-2-hydroxyethylene, thio-2-hydroxytrimethylene, thio-3-hydroxytrimethylene, thio-2-hydroxytetramethylene, thio-3-hydroxytetramethylene, thio-4-hydroxytetramethylene or methylenethio-2-hydroxyethylene radical. These values for —A— are written reading from left to right in formula I such tht the first named part of the radical is attached to ring X and the last named part of the radical is attached to C=D. Thus, for example, when —A— is a 3-hydroxytetramethylene radical, the compound of the formula I contains the part structure III.

A particular value for $R^3$ is a hydrogen atom or a hydroxy, amino, methylamino, 2,2,2-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2-methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroaryl and heteroarylmethyl, in the latter two of which the heteroaryl part is a furan, thiophene, pyrrole, thiazole, oxazole, imidazole, thiadiazole, oxadiazole, triazole, pyrazole, pyridine or pyrimidine ring, and wherein when $R^3$ is or contains a phenyl or heteroaryl ring, that ring is optionally substituted by one or two groups selected from fluorine, chlorine, bromine and iodine atoms and methyl, methoxy, methylthio, dimethylamino, acetyl, trifluoromethyl, hydroxy and amino radicals.

A particular value for the ring formed when $R^3$ and $R^4$ are joind is a pyrrolidine, piperidine, morpholine, piperazine or N-methylpiperazine ring.

The following are 6 preferred features of the guanidine derivative of the formula I. When any one of these features is taken, either singly or in combination, with the other general or particular features of the guanidine derivative of the formula I listed above, there are obtained preferred sub groups of compounds within the above general definition.

1. $R^3$ and $R^4$ atoms.
2. $R^2$ is a hydrogen atom and $R^1$ is a 2,2,2-trifluoroethyl radical.
3. Ring X carries no optional substituent.
4. Ring X is a pyrazole ring.
5. —A— is a 3-hydroxytetramethylene radical.
6. D is an oxygen atom.

A specific compound of the invention is 3-hydroxy-5-(3-[2-(2,2,2-trifluoroethyl)guanidino]-pyrazol-1-yl)valeramide and the pharmaceutically-acceptable acid-addition salts thereof.

A suitable pharmaceutically-acceptable acid addition salt of the guanidine derivative of the formula I is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, $R^4$, A, D and ring X having the meanings stated above, unless indicated otherwise, are therefore provided as further features of the invention.

The process of the invention is characterised by:
(a) reaction of a compound of the formula IV or an activated derivative thereof with a compound of the formula $R^3 R^4 NH$. The activated derivative may, for example, be an ester, for example a 1-6C alkyl ester, for example a methyl or ethyl ester, or an acid halide, for example an acid chloride or acid bromide. Alternatively the activated derivative may be an anhydride, for example a mixed anhydride. Particularly useful mixed anhydrides are those formed by reaction of the compound of the formula IV with a chloroformate, for example ethyl chlorformate or isobutyl chloroformate. The reaction may be conducted in a diluent or solvent such as methanol, ethanol, methylene dichloride, tetrahydrofuran or dimethylformamide and the reaction may be accelerated or completed by the application of heat, for example by heating to the boiling point of the diluent or solvent. When the activated derivative is an acid halide it is advantageous to conduct the reaction in the presence of a base such as triethylamine and to use a non-alcoholic diluent or solvent.

(b) for those compounds in which $R^3$ and $R^4$ are hydrogen atoms and D is an oxygen atom, hydrolysis of a compound of the formula V. The hydrolysis is preferably carried out by use of a strong mineral acid such as concentrated sulphuric acid or by the use of hydrogen peroxide in a basic medium, for example in the presence of sodium hydroxide.

(c) construction of the guanidine radical attached to ring X by reaction of the appropriate thiourea, or a 1–6C S-alkyl (e.g. S-methyl) or S-benzyl derivative thereof, or a salt of such a derivative, with the appropriate amine. The guanidine radical in the compound of the formula I contains three nitrogen atoms each of which carries different substituents. The appropriate amine for use in this reaction may therefore be ammonia, an amine of the formula $R^1R^2NH$ or an amine of the formula VI.

The reaction may be conducted using an excess of one of the reactant as a diluent or solvent, or an additional diluent or solvent, for example methanol or ethanol, may be added. In many cases it is advantageous to use a catalyst such as mercuric oxide, lead oxide or sodium hypochlorite. The reaction may be conducted at ambient temperature or it may be accelerated or completed by the application of heat, for example by heating to the boiling point of the diluent or solvent.

(d) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1R^2NH$ or of the formula VI given above.

(e) for those compounds in which there is a group inserted into A, reaction of a compound of the formula VII or VIII with a compound of the formula IX or X respectively, in which G is an oxygen or sulphur atom or an NH or N-alkyl radical, $R^7$ is a displaceable radical and $A^1$ and $A^2$ are fragments of A, including direct bonds, and are such that $A^1$—G—A falls within the definition of A given above. $R^7$ is, for example, a halogen atom, for example a chlorine, bromine or iodine atom. when $R^7$ is directly attached to ring X $R^7$ may, for example, be a methylsulphinyl or methylsulphonyl radical.

(f) for those compounds in which Z is a nitrogen atom, reaction of a compound of the formula XI with a compound of the formula XII in which $R^7$ is a displaceable radical. $R^7$ is, for example, a halogen atom, for example a chlorine, bromine or iodine atom.

(g) for those compounds in which ring X is a thiazole ring, reaction of a compound of the formula XIII a compound of the formula XIV in which Hal is a chlorine or bromine atom and $R^8$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

The starting material of the formula IV for use in process (a) may be obtained by separate construction of the two side chains on the appropriate ring X. Thus the left-hand side chain may be constructed by reduction of a nitro group to an amino group, reaction of this amino group with an isothiocyanate of the formula $R^1N=C=S$, and finally reaction of the resulting thiourea with ammonia in the presence of mercuric oxide. The method of construction of the right hand side chain may vary depending on the nature of ring X, the nature of the atom in ring X to which A is attached (carbon or nitrogen), the presence or absence of inserted atoms or groups in chain A and the position of the hydroxy radical in chain A. In this construction it may be necessary to protect the acid function as a cyano or ester group and to hydrolyse to the acid as a final step. When A contains no inserted group and Z is a carbon atom, the ring X may be constructed with the right hand chain already in place. Thus when ring X is a thiazole ring a process similar to that described in process (g) may be used. When ring X is a 1,2,3-triazole ring, it may be formed by reaction of methazonic acid with a suitable azide. When ring X is a pyrimidine ring it may be formed by reaction of a suitably-substituted imino ether with 2-chloroacrylonitrile. When there is an inserted group in A, the right hand chain may be built up by a method similar to that described in process (e). When Z is a nitrogen atom, the right hand chain may be formed by a method similar to that described in process (f). In the construction of chain A the hydroxy radical may be introduced by a standard secondary-alcohol-forming reaction, for example as illustrated in the Example.

The starting material of the formula V for use in process (b) may be prepard by methods exactly analogous to the methods of preparation of the compound of the formula IV. Indeed, as already explained, the compound of the formula V may be an immediate precursor of the compound of the formula IV.

The starting material of the formula VI for use in process (e) may be prepared by the methods described above for the preparation of the compounds of the formula IV or V in which the right hand chain is constructed first, followed by use of one of the processes (a) or (b).

The cyanamide, corresponding to the amine of the formula VI, for use in process (d) may be prepared by reaction of the compound of the formula VI with cyanogen bromide.

The starting materials of the formulae VII and VIII for use in process (e), and of the formula IX for use in process (f), may be prepared by construction of the guanidine chain on a suitably substituted ring X.

The starting material of the formula IV for use in process (a) is a particularly useful inermediate for preparing the compounds of the formula I. This starting material, and the activated derivatives (1–6C alkyl ester, acid chloride, acid bromide, mixed anhydride) thereof are therefore provided as a further feature of this invention. Particularly useful mixed anhydrides are those formed with 1–6C alkyl chloroformates, for example ethyl and isobutyl chloroformates.

The starting material of the formula V for use in process (b) is a particularly useful intermediate for preparing the compounds of the formula I. This starting material is therefore provided as a further feature of the invention.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig.

The guinea pig atrium test is carried out as follows:

A guinea pig right atrium is suspended at 1 g. tension (isometric) in a thermostatically-controlled (30−) tissue bath (25 ml.) containing oxygenated (95% $O_2$, 5% $CO_2$) Krebs-Henseleit buffer (pH 7.4). The tissue is allowed to stabilise over 1 hour during which time it is washed 2-4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures.

The compound exemplified in the specification was tested on the guinea pig atrium test and was active below a bath concentration of 10 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, or dogs provided with gastric fistulae or denervated fundic pouches, and whose gastric secretion is stimulated by administration of a secretagogue, for example histamine, pentagastrin, bethanechol or food.

The test in rats is carried out as follows:

Female rats (200-230 g.) are anesthetized by intramuscular administration of urethane (1.5 g./kg.) and the trachea cannulated. A soft tube is passed down the oesophagus into the stomach and secured by a tie in the neck region. A multi-orifice plastic tube (3 mm. diameter) is passed into the antral region of the stomach, via an incision in the duodenum, and tied in place by means of a ligature around the pylorus. Saline (9 g./l NaCl) is perfused through the stomach via the oesophageal cannula at a rate of 7 ml./minute and collected into beakers from the pyloric outlet over Periods of 10 minutes. Acid secretion is stimulated by subcutaneous administration of the specific H-2 agonist dimaprit in a loading dose of 10 mg./kg. followed by an infusion of 30 mg./kg./hour. Acid output is computed by titration of the 10 minute samples to an end point of pH 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO<2%).

The test in dogs provided with chronic fistulae is carried out as follows:

A female pure bred beagle (9-12 kg.) having a chronic gastric fistula is fasted overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mol./kg./hour of histamine or 2 $\mu$g./kg./hour pen agastrin) in saline (15 ml./hour) is begun. Gastric acid samples are collected every 15 minutes. The volume of each sample is measured and a 1 ml. aliquot is titrated to neutrality with 100 mM NaOH to determine acid concentration. When a plateau of secretion is reached (1-2 hours), the test compound is administered intravenously in saline and gastric acid samples are collected for a further 2-3 hours during which time the infusion of the secretagogue continues uninterrupted.

When studying the test compound by the intragastric route, the absence of basal secretion over a period of 30 minutes is ascertained and the test compound, contained in 25 ml. of 0.5% w/v hydroxypropyl methylcellulose and 0.1% w/v 'Tween' 80 in water ('Tween' is a Trade Mark) is instilled into the stomach through a fistula dosing plug. One hour later, the fistula is reopened and intravenous infusion of a secretagogue, as described above, is immediately begun. Gastric acid samples are measured as described above and the approach of acid secretion to a plateau is compared to that of a control animal which is dosed intragastrically only with the dosing vehicle.

When studying the test compound by the oral route it is administered in a gelatin capsule with 15 ml. of water. One hour later, the fistula is opened and intravenous infusion of the secretagogue is immediately begun. Gastric acid samples are measured as above and the approach of acid secretion to a plateau is compared to that of an undosed control animal.

The test in dogs provided with denervated fundic pouches is carried out as follows:

Male beagle dogs (14-22 kg.) are prepared with vagally denervated pouches of the fundic gland area by the method of Rudick et al. (*J.Surg.Res.*, 1967, 7, 383). The animals are allowed 4-6 weeks to recover from surgery and a further period of 2-3 months prior to routine use, to allow for table training and standardization of secretory responses. The dogs are starved for 23 hours before use (water ad lib) and during experiments they are lightly restrained in cloth slings. After rinsing the pouch with warm water, histamine is infused subcutaneously at a rate of 10 $\mu$g./minute. This dose of agonist produces a submaximal (60-90% of maximum) increase in acid output in all dogs used. Pouch secretions are collected over 15 minute periods into graduated glass test-tubes and the volume measured to the nearest 0.1 ml. A 500 $\mu$l. sample is diluted with 5 ml. of saline and titrated to pH 7.0 with 100 mM.NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the atrium test are predictive of activity in the rat and dog tests.

No overt toxicity or side effects were noted during the rat or dog test.

The N-methylcyanoguanidine group in known H-2 receptor antagonists is potentially changeable into the mutagenic N-nitroso N-methylcyanoguanidine group in the mammalian body (Pool et al., *Toxicology*, 1979, 15, 69). The corresponding group in the compounds of the present invention, $CONR^3R^4$, is not potentially changeable into carcinogenic nitroso derivatives when $R^3$ and $R^4$ are hydrogen atoms.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide - magnesium hydroxide mixtures; antipepsin compounds, for example pepstatin; other histamine H-2 antagonists, for example cimetidine or ranitidine; ulcer healing agents, for example carbenoxolone or bismuth salts; anti-inflammatory agents, for example ibuprofen, indomethacin, naproxen or asprin; prostaglandins, for example 16, 16-dimethylprostaglandin $E_2$; classical antihistamines (histamine H-1 antagonists), for example mepyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1-10% w/w of the guanidine derivative of the invention. A preferred pharmaceutical composition of the invention is one suitable for oral administration in unit dosage form, for example a tablet or capsule which contains between 5 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between 5 mg. and 500 mg., and preferably between 10 mg. and 100 mg., of guanidine derivative or an intravenous, subcutaneous or intramuscular dose of between 0.5 mg. and 50 mg., and preferably between 2 mg. and 20 mg., of the guanidine derivative, the composition being administered 1 to 4 times, and preferably once, per day. The rectal dose will be approximately the same as the oral dose. The composition may be administered less frequently when it contains an amount of guanidine derivativr which is a multiple of the amount which is effective when given 1–4 times per day.

The invention is illustrated, but not limited, by the following Example. The n.m.r. spectra are quoted in $\delta$ relative to tetramethylsilane ($\delta = 0$) as internal standard (s=singlet, d=doublet, t=triplet, q=quartet, m=multiplet, br=broad). The temperatures are in degrees Centigrade. The following contractions are used:

DMF=dimethyl formamide
MeOH=methanol
EtOH=ethanol
THF=tetrahydrofuran
EtOAc=ethyl acetate
DMSO=dimethylsulphoxide Attention is drawn to the fact that 3-nitropyrazole is an explosion harzard.

EXAMPLE

Methyl 3-hydroxy-5-(3-[2-(2,2,2-trifluoroethyl)-guanidino]pyrazol-1-yl)valerate (0.7 g.) was stirred in concentrated aqueous ammonia (d 0.88, 10 ml.) for 17 hours at 20°. Volatile material was evaporated in vacuo and the residue was purified by chromatography on 4 silica coated plates (40 cm.×20 cm.) eluted with triethylamine/EtOH/EtOAc 1:2:9 v/v/v. The product, which had an $R_f$ value of 0.2–0.3, was extracted with MeOH and the extract evaporated in vacuo to a friable glass. There was thus obtained 3-hydroxy-5-(3-[2-(2,2,2-trifluoroethyl)guanidino]pyrazol-1-yl)valeramide (0.38 g.) having the following n.m.r. spectrum in $D_2O$: 7.52 (d, 1H); 5.92 (d, 1H); 3.82–4.22 (m, 5H); 2.42 (d, 2H); 1.82–2.12 (m, 2H). The mass spectrum showed a mass ion (M+) at 322 and further ions at 278, 234, 220 and 96.

The starting material may be prepared as follows:

A solution of 3-nitropyrazole (22.6 g.) in dry DMF (25 ml.) was added dropwise over 30 minutes to a suspension of sodium hydride (5.28 g.) in dry DMF (50 ml.) at 0°. The mixture was stirred for 30 minutes, ethyl 3-bromopropionate (36.8 g.) was added over 10 minutes, the mixture was kept at −15° for 17 hours and then allowed to warm to 20°. Water (550 ml.) was added, the solution was extracted with EtOAc (4×100 ml.) and the combined extracts were dried ($MgSO_4$) and evaporated in vacuo to an oil. Fractionation on a silica medium pressure liquid chromatography column eluted with EtOAc/petrol (b.p.60°–80°) 1:1 v/v gave ethyl 3-(3-nitropyrazol-1-yl)propionate (19.2 g.) as a low melting solid. The n.m.r. spectrum in $CDCl_3$ included the following resonances: 7 6 (d, 1H); 6.85 (d, 1H); 4.5 (t, 2H); 4.1 (q, 2H); 2.95 (t, 2H); 1.2 (t, 3H).

Part of the above ester (2.13 g.) was stirred in dry toluene (50 ml.) at −75° and di-isobutyl aluminium hydride (7.0 ml. of a 1.7M solution in toluene) was added over 15 minutes at −75°. The mixture was stirred at −75° for a further 15 minutes then allowed to warm to 20°. Water (500 ml.) and EtOAc (150 ml.) was added and the organic layer was separated. The aqueous layer was filtered and further extracted with EtOAc (4×100 ml.). The combined organic layers were dried ($MgSO_4$) and evaporated to give crude 3-(3-nitropyrazol-1-yl)propionaldehyde (1.75 g.) as an oil which was used in the next stage without further purification. The n.m.r. spectrum in $d_6DMSO$ included the following resonances: 9.75 (s, 1H); 8.05 (d, 1H); 7.0 (d, 1H); 4.5 (t, 2H); 3.2 (t, 2H).

Lithium bis(trimethylsilyl)amide (10 ml. of a 1M solution in THF) was cooled to −75° under argon and freshly distilled EtOAc (0.88 g.) was added over 5 minutes. Crude 3-(3-nitropyrazol-1-yl)propionaldehyde (1.75 g.) in dry THF (10 ml.) was added at −75° over 10 minutes and the mixture was kept at −75° for a further 15 minutes then allowed to warm to 20°. Water (200 ml.) was added and the mixture was extracted with EtOAc (3×60 ml.). The extracts were dried (MgSO₄) and evaporated in vacuo to give crude ethyl 3-hydroxy-5-(3-nitropyrazol-1-yl)valerate as an oil (2.41 g.) which was used in the next stage without further purification. The n.m.r. spectrum in CD₃OD included the following resonances: 7.76 (d, 1H): 6.86 (d, 1H); 4.36 (t, 2H); 4.1 (q, 2H); 3.9 (m, 1H); 2.47 (d, 2H); 2.1 (m, 2H); 1.24 (t, 3H).

A solution of the above crude ethyl 3-hydroxy-5-(3-nitropyrazol-1-yl)valerate (2.41 g.) in MeOH (250 ml.) was hydrogenated over 5% w/w Pd/carbon (0.3 g.) at atmospheric pressure over 2 hours. Uptake was 650 ml. The catalyst was filtered off and the filtrate was evaporated in vacuo to give ethyl 3-hydroxy-5-(3-aminopyrazol-1-yl)valerate as an oil (1.47 g.).

To a solution of the above aminoester (1.47 g.) in dry dioxan (15 ml.) was added 2,2,2-trifluoroethyl isothiocyanate. The mixture was stirred at 20° for 17 hours, filtered and evaporated in vacuo to an oil (1.9 g.). The oil was purified on a silica medium pressure liquid chromatography column eluted with EtOAc/petroleum ether (b.p. 60°-80°) 1:3 v/v to give ethyl 3-hydroxy-5-(3-[3-(2,2,2-trifluoroethyl)thioureido]pyrazol-1-yl)valerate. The n.m.r. spectrum in CD₃OD included the following resonances: 7.54 (d, 1H); 5.92 (d, 1H); 4.6 (q, 2H); 3.8–4.4 (m, 5H); 2.48 (d, 2H); 2.02 (m, 2H); 1.28 (t, 3H).

To a solution of the above thioureidoester (0.9 g.) in MeOH saturated with ammonia (25 ml.) was added mercuric oxide (0.9 g.). The mixture was stirred at 20° for 2 hours then centrifuged. The supernatant was evaporated in vacuo to give methyl 3-hydroxy-5-(3-[2-(2,2,2-trifluoroethyl)guanidino]pyrazol-1-yl)valerate as an oil. The n.m.r. spectrum in CD₃OD included the following resonances: 7.36 (d, 1H); 5.81 (d, 1H); 4.14 (t, 2H); 4.0 (q, 2H); 3.68 (s, 3H); 2.46 (d, 2H); 1.94 (m, 2H).

GUANIDINE DERIVATIVES FORMULAE

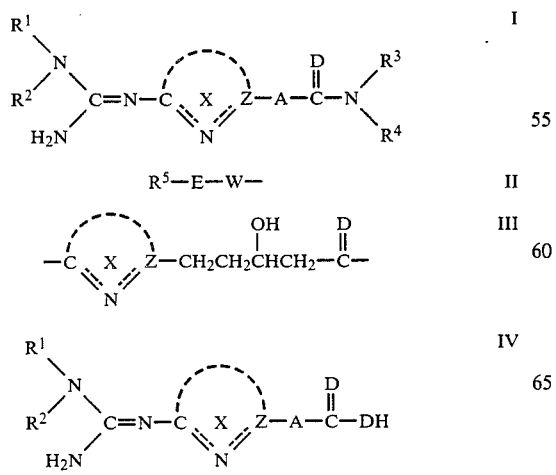

I

II  R⁵—E—W—

III

IV

GUANIDINE DERIVATIVES FORMULAE -continued

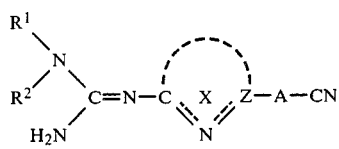

V

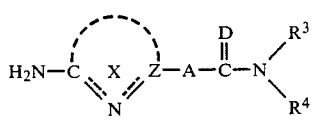

VI

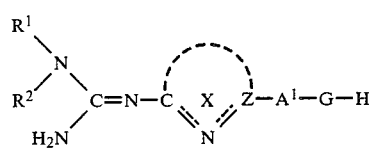

VII

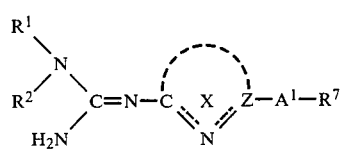

VIII

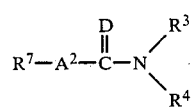

IX

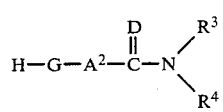

X

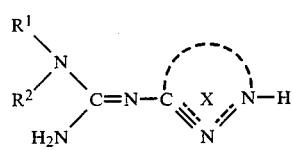

XI

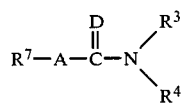

XII

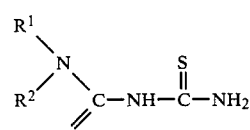

XIII

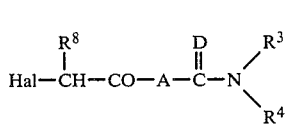

XIV

We claim:

1. A guanidine derivative of the formula I:

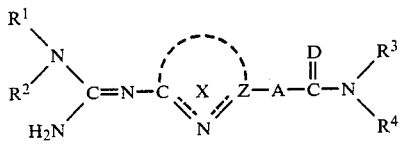

in which
R[1] and R[2], which may be the same of different, are hydrogen atoms or branched or unbranched 1–10C alkyl, 3–8C cycloalkyl or 4–14C cycloalkylalkyl radicals, each alkyl, cycloalkyl or cycloalkylalkyl radical being optionally substituted by one or more halogen atoms selected from fluorine, chlorine and bromine atoms, provided that at least one of R[1] and R[2] is a halogen-substituted alkyl, cycloalkyl or cycloalkylalkyl radical and provided there is no halogen substituent on the carbon atom of the alkyl, cycloalkyl or cycloalkylalkyl radical which is directly attached to the nitrogen atom, or R[2] is a hydrogen atom and —R[1] is a radical of the formula II:

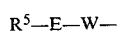

in which W is an unbranched 2–6C alkylene chain which is optionally substituted by one or two 1–4C alkyl radicals, E is an oxygen or suphur atom, a sulphinyl or sulphonyl radical, or a radical of the formula NR[6] in which R[6] is a hydrogen atom or a 1–6C alkyl radical, R[5] is a hydrogen atom or an unbranched 1–6C alkyl radical which is optionally substituted by one or two 1–4C alkyl radicals, or R[5] and R[6] are joined to form, together with the nitrogen atom to which they are attached, a pyrrolidine, piperidine, morpholine, piperazine or N-methylpiperazine ring;

in ring X the dotted line is a double bond on one side of the nitrogen atom and Z is a carbon or nitrogen atom such that ring X is pyrazole or imidazole wherein said ring X may, where possible, carry one or two optional substituents, the optional substituents, on ring X being selected from fluorine, chlorine and bromine atoms and 1–6C alkyl, 1–6C alkoxy, trifluoromethyl, hydroxy and amino radicals;

—A— is a 3–8C alkylene chain which is substituted by a hydroxy radical and into which is optionally inserted, as part of the backbone of the chain, one or two groups selected from oxygen and sulphur atoms and NH and 1–6C N-alkyl radicals, provided that the shortest link between ring X and C=D is of at least 3 atoms, provided that no optional insertion is made in chain A which results in the inserted group being directly attached to C=D provided that no two insertions are directly attached one to the other, and provided that an inserted atom or radical is not attached to the carbon atom which carries the hydroxy radical;

D is an oxygen or sulphur atom;
R[3] is a hydrogen atom or a hydroxy, amino, 1–6C alkylamino, 1–6C haloalkylamino, 1–6C alkanoylamino, 1–6C alkyl, 3–8C cycloalkyl, 4–12C cycloalkylalkyl, 2–6C alkenyl, 2–6C alkynyl, 1–6C haloalkyl, 1–6C alkoxy, 1–6C hydroxyalkyl, 2–10C alkoxyalkyl, 2–10C alkylthioalkyl, 1–6C aminoalkyl, 2–8C alkylaminoalkyl, 3–12C dialkylaminoalkyl, 2–8C alkanoylaminoalkyl, 8–14C benzoylaminoalkyl, 3–10C alkoxycarbonylalkyl, 2–8C carbamoylalkyl, phenyl, 7–11C phenylalkyl, heteroaryl or heteroarylalkyl radicals, wherein the heteroaryl part is a furan, thiophene, pyrrole, thiazole, oxazole, imidazole, thiadiazole, oxadiazole, triazole, pyrazole, pyridine or pyrimidine ring, wherein the alkyl part of the heteroarylalkyl radical is 1–6C and wherein, when R[3] is a phenyl or heteroaryl ring, that ring is optionally substituted by one or two groups selected from fluorine, chlorine, bromine and iodine atoms and 1–6C alkyl, 1–6C alkoxy, 1–6C alkylthio, 2–6C dialkylamino, 2–6C alkanoyl, trifluoromethyl, hydroxy and amino radicals;

R[4] is a hydrogen atom; or R[3] and R[4] are joined to form, together with the nitrogen atom to which they are attached, a 5-6- or 7-membered saturated ring which optionally contains a double bond or an additional oxygen atom, NH or 1–6C N-alkyl radical;

and a pharmaceutically-acceptable acid-addition salt thereof.

2. A guanidine derivative of the formula I:

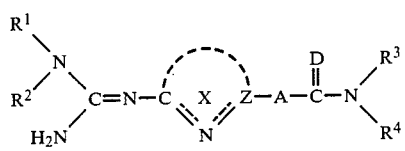

in which
R[1] and R[2] are each selected from the group consisting of hydrogen atoms and 2,2,2-trifluoroethyl, 2,2,2-trichloroethyl, 2-chloro-2,2-difluoroethyl, 2,2-dichloro-2-fluoroethyl, 2-bromo-2,2-difluoroethyl, 2,2-dibromo-2-fluoroethyl, 2-fluoroethyl, 2-chloroethyl, 2,2-difluoroethyl, 2,2-dichloroethyl, 2-chloro-2-fluoroethyl, 2-bromo-2-fluoroethyl, 2,2,3,3-tetrafluoropropyl, 2,2,3,3,3-pentafluoropropyl, 1,1,1,3,3,3-hexafluoroisopropyl, 1,3-dichloro-1,1,3,3-tetrafluoroisopropyl, 1-chloro-1,1,3,3,3-pentafluoroisopropyl, 1,3-difluoroisopropyl, 2,2,3,3,4,4,4-heptafluorobutyl, 2,2,3,3-tetrafluorocyclopropyl, 2-chloro-2,3,3-trifluorocyclopropyl, 2,2-difluorocyclopropyl, 2-chloro-3,3-difluorocyclopropyl, 2,2,3,3,4,4-hexafluorocyclobutyl, 2-chloro-2,3,3,4,4-pentafluorocyclobutyl, (1,2,2,3,3-pentafluorocyclopropyl)methyl, (2-chloro-1,2,3,3-tetrafluorocyclopropyl)methyl, (1,2,2,3,3,4,4-heptafluorocyclobutyl)methyl, (2-chloro-1,2,3,3,4,4-hexafluorocyclobutyl)methyl, methyl, ethyl, propyl, isopropyl, butyl, cyclopropyl, cyclobutyl, cyclopropylmethyl and cyclobutylmethyl radicals, provided that at least one of R[1] and R[2] is a halogen-substituted radical, or R[2] is a hydrogen atom and R[1] is 2-methoxyethyl, 2-hydroxyethyl, 2-methylthioethyl or 2-dimethylaminoethyl radical;

ring X is an oxazole, thiazole, imidazole, 1,2,4-thiadiazole, 1,2,4-oxadiazole, 1,2,3-triazole, 1,2,4-triazole, pyrazole, pyrazine, pyridine, pyrimidine or 1,3,5-triazine ring, each being optionally substituted, where possible, by one or two substituents selected from fluorine, chlorine and bromine atoms and methyl, methoxy, trifluoromethyl, hydroxy and amino radicals;

—A— is a 1-hydroxytrimethylene, 2-hydroxytrimethylene, 3-hydroxytrimethylene, 1-hydroxytetramethylene, 2-hydroxytetramethylene, 3-hydroxytetramethylene, 4-hydroxytetramethylene, 1-hydroxypentamethylene, 2-hydroxypentamethylene, 3-hydroxypentamethylene, 4-hydroxypentamethylene, 5-hydroxypentamethylene, thio-2-hydroxyethylene, thio-2-hydroxytrimethylene, thio-3-hydroxytrimethylene, thio-2-hydroxytetranethylene, thio-3-hydroxytetramethylene, thio-4-hydroxytetramethylene or methylenethio-2-hydroxyethylene radical;

D is an oxygen or sulphur atom;

$R^3$ is a hydrogen atom or a hydroxy, amino, methylamino, 2,2,2-trifluoroethylamino, acetylamino, methyl, cyclohexyl, cyclohexylmethyl, allyl, propargyl, 2,2,2-trifluoroethyl, methoxy, 2-hydroxyethyl, 2-methoxyethyl, 2-methylthioethyl, 2-aminoethyl, 2-methylaminoethyl, 2-dimethylaminoethyl, 2-acetylaminoethyl, 2-benzoylaminoethyl, methoxycarbonylmethyl, 2-carbamoylpropyl, phenyl, benzyl, heteroaryl or heteroarylmethyl radical, in the latter two of which the heteroaryl part is a furan, thiophene, pyrrole, thiazole, oxazole, imidazole, thiadiazole, oxadiazole, triazole, pyrazole, pyridine or pyrimidine ring, and wherein when $R^3$ is or contains a phenyl or heteroaryl ring, that ring is optionally substituted by one or two groups selected from fluorine, chlorine, bromine and iodine atoms and methyl, methoxy, methylthio, dimethylamino, acetyl, trifluoromethyl, hydroxy and amino radicals;

$R^4$ is a hydrogen atom; or $R^3$ and $R^4$ are joined to form, together with the nitrogen atom to which they are attached, a pyrrolidine, piperidine, morpholine, piperazine or N-methylpiperazine ring; and the pharmaceutically-acceptable acid-addition salts thereof.

3. A guanidine derivative as claimed in claim 1 in which $R^3$ and $R^4$ are hydrogen atoms.

4. A guanidine derivative as claimed in claim 2 in which $R^3$ and $R^4$ are hydrogen atoms.

5. A guanidine derivative as claimed in claim 1 in which $R^2$ is a hydrogen atom and $R^1$ is a 2,2,2-trifluoroethyl radical.

6. A guanidine derivative as claimed in claim 2 in which $R^2$ is a hydrogen atom and $R^1$ is a 2,2,2-trifluoroethyl radical.

7. A guanidine derivative as claimed in claim 3 in which $R^2$ is a hydrogen atom and $R^1$ is a 2,2,2-trifluoroethyl radical.

8. A guanidine derivative as claimed in claim 1 in which D is an oxygen atom and ring X is an unsubstituted pyrazole ring.

9. A guanidine derivative as claimed in claim 2 in which D is an oxygen atom and ring X is an unsubstituted pyrazole ring.

10. A guanidine derivative as claimed in claim 3 in which D is an oxygen atom and ring X is an unsubstituted pyrazole ring.

11. A guanidine derivative as claimed in claim 4 in which D is an oxygen atom and ring X is an unsubstituted pyrazole ring.

12. The compound 3-hydroxy-5-(3-[2-2,2,2-trifluoroethyl) guanidino]pyrazol-1-yl) valeramide, and a pharmaceutically-acceptable acid-addition salt thereof.

13. A pharmaceutical composition useful to inhibit gastric acid secretion comprising an effective amount of a guanidine derivative as claimed in claim 1 in association with a pharmaceutically-acceptable diluent or carrier.

14. A method of inhibiting gastric acid secretion in a warm-blooded animal comprising administering to the warm-blooded animal the pharmaceutical composition as defined in claim 13.

* * * * *

UNITED STATES PATENT AND TRADEMARK OFFICE
CERTIFICATE OF CORRECTION

PATENT NO. : 4,683,228

DATED : JULY 28, 1987

INVENTOR(S) : KIRKLAND ET AL

It is certified that error appears in the above-identified patent and that said Letters Patent is hereby corrected as shown below:

In The Title:

"GUANIDINOPYRAZOLYLAMIDES, GUANIDIMOIMIDAZOLYLAMIDES, COMPOSITIONS CONTAINING THEM, AND METHOD OF USING THEM TO INHIBIT GASTRIC ACID SECRETION" should read --GUANIDINOPYRAZOLYLAMIDES, GUANIDINOIMIDAZOLYLAMIDES, COMPOSITIONS CONTAINING THEM, AND METHOD OF USING THEM TO INHIBIT GASTRIC ACID SECRETION--.

In The Specification:

Column 1, line 37, after "in which" insert --:--.
Column 2, line 25, "2-carbamoylalkyl" should read --2-8C carbamoylalkyl--.
Column 2, line 25, "6-10 aryl" should read --6-10C aryl--..
Column 4, line 24, before "atoms" insert --are hydrogen--.
Column 4, line 35, "acid addition" should read --acid-addition--.
Column 5, line 52, after "XIII" and before "a", insert --with--.
Column 8, line 9, "pen agastrin" should read --pentagastrin--.
Column 10, line 5, "derivativr" should read --derivative--.
Column 10, line 21, "harzard" should read --hazard--.
Column 10, line 54, "7 6" should read --7.6--.

UNITED STATES PATENT AND TRADEMARK OFFICE
CERTIFICATE OF CORRECTION

PATENT NO.   : 4,683,228
DATED        : July 28, 1987
INVENTOR(S)  : KIRKLAND ET AL It is certified that error appears in the above-identified patent and that said Letters Patent is hereby corrected as shown below:

In The Claims:

Claim 1, column 13, line 10, "of" should read —or—.
Claim 1, column 13, line 43, delete "," after "ents".
Claim 2, column 15, line 10, "ranethylene" should read —ramethylene—.
Claim 12, column 16, line 26, "3-hydroxy-5-(3-[2-2,2,2-trifluoro-" should read —3-hydroxy-5-(3-[2-(2,2,2-trifluoro —.

Signed and Sealed this

Seventh Day of March, 1989

Attest:

DONALD J. QUIGG

*Attesting Officer*   *Commissioner of Patents and Trademarks*